(12) United States Patent
Brumeanu et al.

(10) Patent No.: US 6,811,785 B2
(45) Date of Patent: Nov. 2, 2004

(54) MULTIVALENT MHC CLASS II—PEPTIDE CHIMERAS

(75) Inventors: Teodor Doru Brumeanu, New York, NY (US); Sofia Casares, New York, NY (US); Constantin A. Bona, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 174 days.

(21) Appl. No.: 09/850,336

(22) Filed: May 7, 2001

(65) Prior Publication Data

US 2002/0164340 A1 Nov. 7, 2002

(51) Int. Cl.⁷ .......................... A61K 39/44; C07K 16/46
(52) U.S. Cl. ............... 424/194.1; 530/391.9; 530/323; 530/391.5
(58) Field of Search ............... 424/193.1, 194.1; 530/323, 391.5, 391.9

(56) References Cited

U.S. PATENT DOCUMENTS

| | | | |
|---|---|---|---|
| 6,015,884 A | * | 1/2000 | Schneck et al. |
| 6,106,840 A | | 8/2000 | Clark et al. |
| 6,197,302 B1 | | 3/2001 | Hirsch et al. |
| 6,211,342 B1 | | 4/2001 | Hirsch et al. |

FOREIGN PATENT DOCUMENTS

| | | | |
|---|---|---|---|
| WO | | 9310220 | 5/1993 |
| WO | | 9636357 | 11/1996 |
| WO | WO 96/40731 | * | 12/1996 |
| WO | | 9909064 | 2/1999 |

OTHER PUBLICATIONS

Casares et al., "Antigen–specific Signaling by a Soluble, Dimeric Peptide/Major Histocompatibility Complex Class II/Fc Chimera Leading to T Helper–Cell Type 2 Differentiation", J. Exp. Med, vol. 190, No. 4, Aug. 16, 1999, pp. 543–553.

* cited by examiner

Primary Examiner—Christina Chan
Assistant Examiner—F. Pierre Vandervegt
(74) Attorney, Agent, or Firm—Marshall, Gerstein & Borun LLP

(57) ABSTRACT

The present invention provides a multimeric complex of at least two chimeric molecules, wherein the chimeric molecules comprise an immunoglobulin constant region element and two MHC elements wherein each MHC element is associated with a peptide, and wherein the chimeric molecules are covalently linked through a carbohydrate residue of the immunoglobulin constant region element by a polyalkylene glycol linker. Methods of making and using the multimeric complexes are also provided.

15 Claims, 5 Drawing Sheets

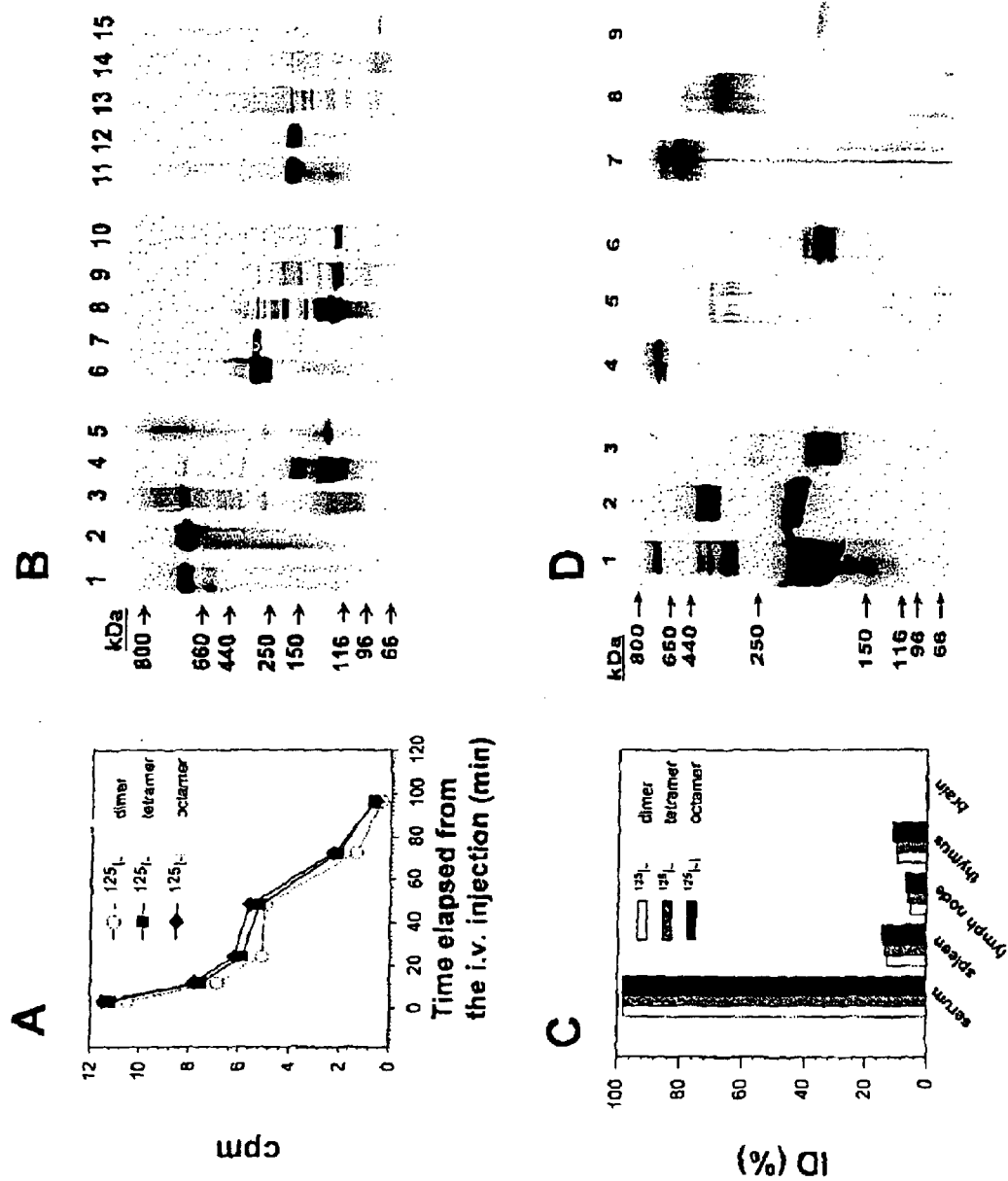
Figures 3A-D

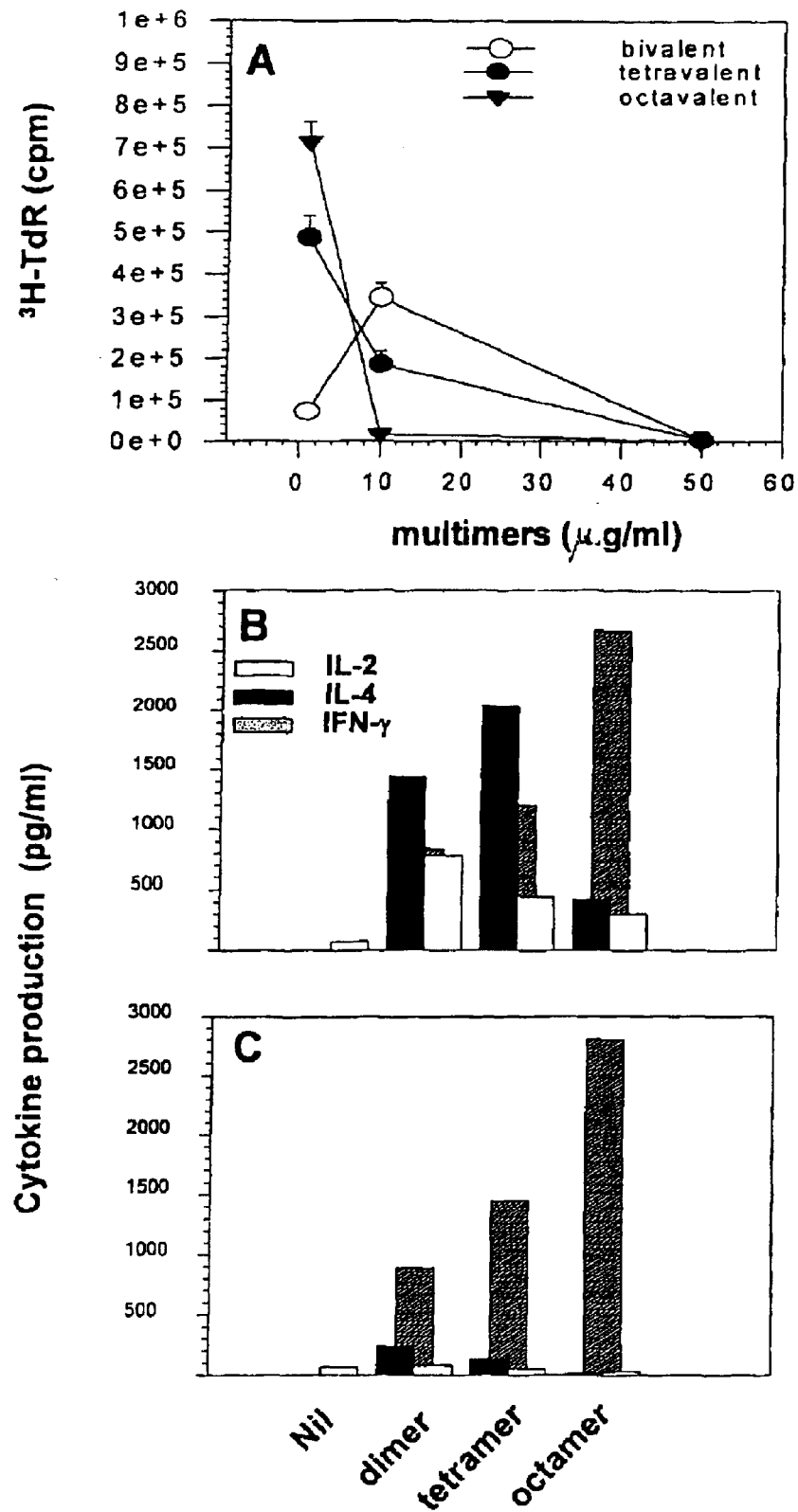
Figures 4A-C

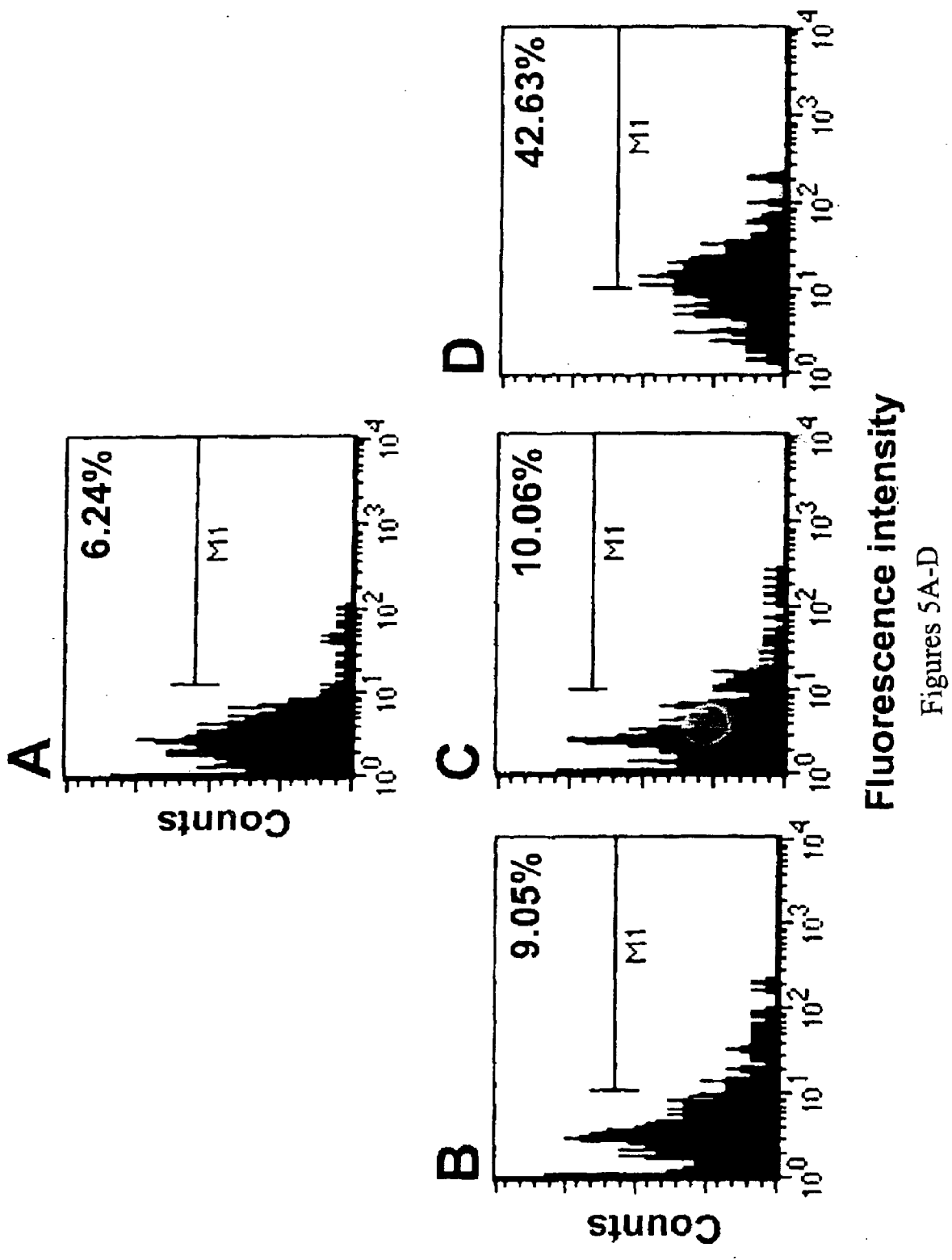
Figures 5A-D

MULTIVALENT MHC CLASS II— PEPTIDE CHIMERAS

BACKGROUND OF THE INVENTION

T cells respond to antigens in the context of major histocompatability complex ("MHC") molecules. Cytotoxic T cells respond to antigens in the context of MHC class I molecules, while helper T cells respond to antigens in the context of MHC class II molecules (for review, see Davies, H., 1997, *Introductory Immunobiology*, Chapman & Hall, New York, pp. 177–223). Class I molecules are comprised of a heavy α chain and a $\beta_2$-microglobulin light chain; class II molecules are heterodimers comprised of α and β chains, each having two domains and being of approximately the same length. The DNA regions containing MHC genes have been well characterized for mouse and man. The mouse MHC is referred to as the "H-2 complex" and the human MHC is referred to as the "HLA complex" (for Human Leukocyte Antigen). Class I molecules are encoded at the A, B and C loci in man and the K, D, and L loci in mouse. Class II molecules are encoded at the DP, DQ and DR regions in man and the I-A and I-E regions in mouse. At each region, a multitude of alleles has been identified.

The interaction between MHC-peptide complexes expressed on antigen presenting cells (APC) and T cell receptors (TCR) expressed on T cells leads to various T cell functions including proliferation and cytokine secretion, differentiation toward various cell subsets, anergy and apoptosis. See Davis et al. (1998) Ann. Rev. Immunol. 16:523–544. Various attempts have been made to mimic these immunomodulatory effects with soluble MHC-peptide complexes. For example, MHC molecules have been extracted from cell membranes and subjected to peptide elution followed by exchange for specific peptides in vitro. (Nag et al. (1996) Cell. Immunol. 170:25–33; Sharma et al. (1991) Proc. Natl. Acad. Sci. U.S.A. 88:11465–11469; Spack et al. (1995) J. Autoimmunity 8:787–807). Also, MHC molecules have been produced recombinantly and then loaded with peptides in vitro (Abastado et al. (1995) J. Exp. Med. 182: 439–447; Altman et al. (1996) Science 274: 94–96; Godeau et al. (1992) J. Biol. Chem. 267:24223–24229; Scheirle et al. (1992) J. Immunol. 149:1994–1999; Scott et al. (1996) J. Exp. Med. 183:2087–2095; Stem et al. (1992) Cell 68:465–477). Other attempts include the production of genetically engineered, covalently-linked peptide/MHC chimeras (International Patent Application Publication No. WO95/23814; Kozono et al. (1994) Nature 369:151–154; Mottez et al. (1995) J. Exp. Med. 181:493–502; Rhode et al. (1996) J. Immunol. 15:4885–4891; and U.S. Pat. No. 5,869,270).

A major disadvantage of monovalent MHC II-peptide ligands is that they are recognized by cognate TCRs with low avidity. The on-rates at 25° C. vary from very slow (1,000) to moderately fast (200,000), whereas the off-rates are in a relative narrow range (0.5–0.01), or to a $t_{1/2}$ of 12–30 seconds. Rates are estimated to be 2–3 times faster at physiologic temperature (Matsui et al. (1991) Science 254:1788–1791; Matsui et al. (1994) Proc. Nat. Acad. Sci. USA 91:12862–12866). In general, TCR exhibits 2 to 3-times lower binding affinity for the monovalent MHC II-peptide complex than for clonotypic antibodies to MHC-peptide complexes (Porgador et al. (1997) Immunity 6:715–726; Dadaglio et al. (1997) Immunity 6:727–738).

Recently, multivalent MHC II-peptide ligands with increased avidity for the cognate TCRs have been generated. A soluble bivalent MHC-II peptide ligand on an immunoglobulin scaffold, which binds stably and specifically to cognate TCR on T-cells, has been engineered. (Casares et al. (1997) Protein Engineering 10:1295–1301; International Patent Application Publication No. WO99/09064). Bivalent MHC II-peptide ligands engineered on an immunoglobulin scaffold exhibit approximately 20 to 25 times lower off-rates than the monovalent forms (Appel et al. (2000) J. Biol. Chem. 275:312–321). U.S. Pat. No. 6,211,342 discloses divalent MHC complexes that may be loaded with a peptide. Reich et al. expressed a BirA-dependent biotinylation site on β-chain of MHC class II molecules to engineer tetravalent MHC II-peptide ligands through the streptavidin-mediated cross linking (Reich et al. (1997) Nature 387:617–620). Tetravalent MHC II/peptide ligands were successfully used to identify low-frequency antigen-specific T-cells in the peripheral blood of patients with HIV infection (Crawford et al. (1998) Immunity 8:675–682). However, the tetravalent MHC II/peptide ligands did not exceed the avidity of immunoglobulin-based, dimeric MHC II/peptide ligands, presumably because of the rigidity of biotin-streptavidin bonds that may not provide optimal accommodation of the tetramers on the TCR motifs.

Although the tetrameric MHC II-peptide molecules generated through the biotin-streptavidin bonds are valuable tools for in vitro investigation, the non-covalent nature of this bonds raises the concern of its stability in vivo. Accordingly, there is a need in the art for multimeric MHC II-peptide molecules that maintain structural integrity in vivo and exhibit immunomodulatory effects on T cells.

SUMMARY OF THE INVENTION

The present invention provides a complex comprising at least two chimeric molecules, wherein each chimeric molecule comprises an immunoglobulin constant region element having two heavy chains, wherein each heavy chain is linked to an MHC element, and wherein a peptide of interest is associated with each of the MHC elements, and wherein at least two of the chimeric molecules are covalently linked through a carbohydrate residue of the immunoglobulin constant region element by a polyalkylene glycol linker.

The present invention further provides compositions comprising the complexes.

In another embodiment, the present invention is directed to a method of making such a complex.

The present invention also provides a method of modulating T cell function comprising administering the complex of the invention, and a method of diagnosing an autoimmune disorder using the complex of the invention.

BRIEF DESCRIPTION OF THE DRAWINGS

FIGS. 3A–D provide results of studies demonstrating the life span of the multimeric complexes in blood circulation and distribution in lymphoid organs.

FIGS. 4A–C are graphs demonstrating thymidine incorporation and cytokine production in TCR-HA T cells exposed to various concentrations of multimers.

FIGS. 5A–D show the results of FACS analysis used to determine the percent of apoptosis of T cells after exposure to multimers.

DETAILED DESCRIPTION OF THE INVENTION

Figure 1:
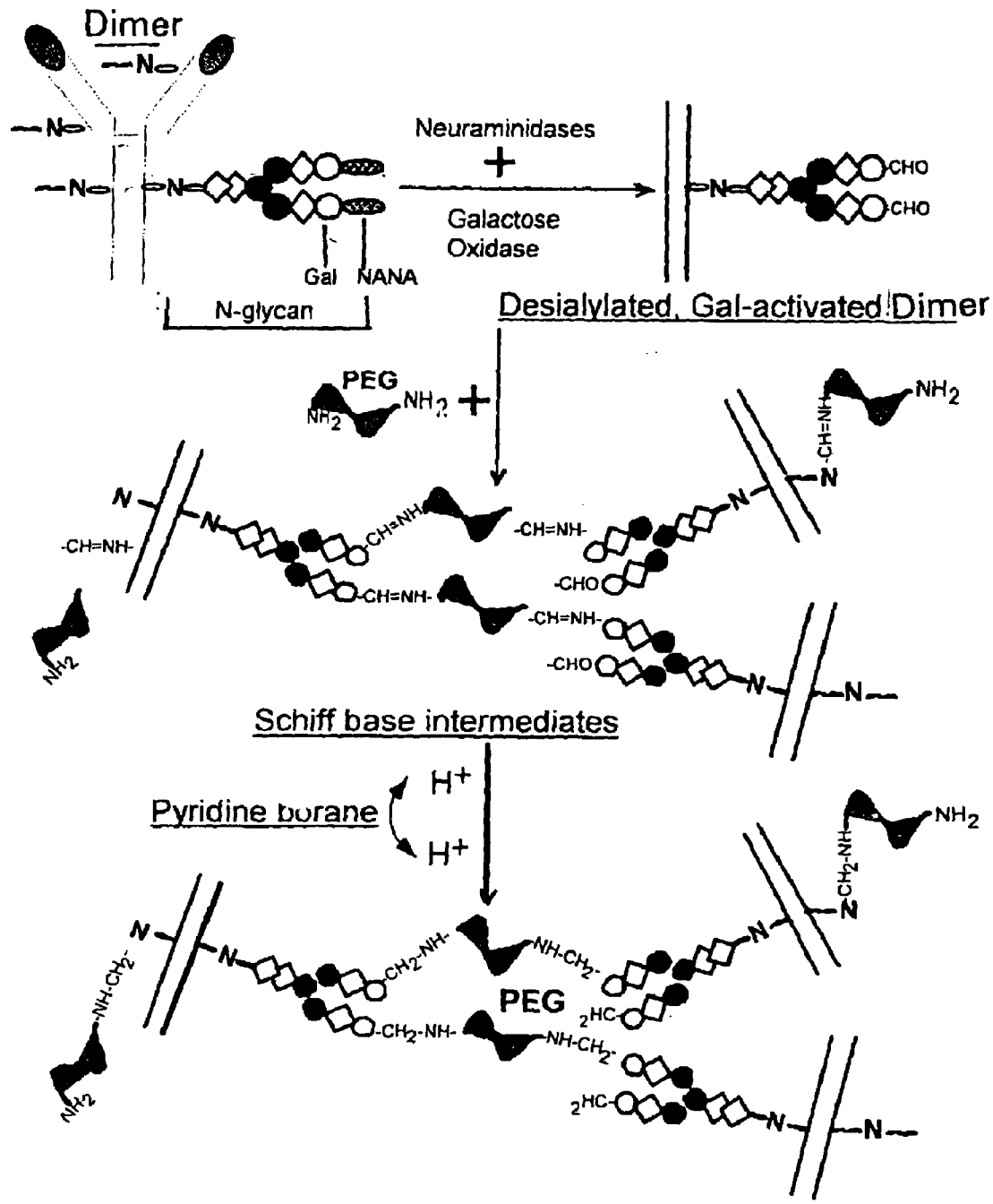
FIG. 1 depicts a reaction scheme for producing the multimeric complexes of the present invention.

The present invention provides multimeric complexes of at least two chimeric molecules, wherein the chimeric molecules comprise an immunoglobulin constant region element and two MHC elements, wherein each of the MHC elements is associated with a peptide of interest. The chimeric molecules contained in the complex are referred to herein as divalent in that they contain two MHC-peptide moieties. The chimeric molecules are covalently linked through a carbohydrate residue of the immunoglobulin constant region element by a polyalkylene glycol linker to provide the multimeric complexes of the present invention. In a preferred embodiment two divalent chimeric molecules are linked to provide a tetrameric complex. In another preferred embodiment, four divalent chimeric molecules are linked to provide an octameric complex.

The immunoglobulin constant region element of the chimeric molecule is a portion of an immunoglobulin molecule comprising all or part of the C-terminal portion of both heavy chains wherein one heavy chain constant region component is joined to the other by one or more disulfide bonds. The immunoglobulin constant region element is alternatively referred to herein as an Fc element, even though the term is not herein restricted to the product resulting from papain digestion of an immunoglobulin molecule. Preferably, the immunoglobulin constant region element comprises the CH3 and CH2 domains and all or a portion of the hinge region. The hinge region may comprise the required disulfide bond.

The MHC element may be class I or class II, and preferably comprises all or part of the extracellular portions of the chains. In a preferred embodiment, the MHC element comprises the extracellular domains of the α and β chains of an MHC class II molecule.

The MHC class II element may be human or non-human, and may be selected to be of the same species as an intended recipient of the complex of the invention. Examples of human MHC class II elements include DP, DQ and DR molecules and portions thereof, for which numerous alleles are known. Particularly preferred are MHC class II elements associated with particular autoimmune conditions: for example, DR3, DQw2 and DR4, DQw8 (associated with insulin dependent diabetes mellitus (IDDM); DR4, DQw3 and DR1, DQw1 (associated with rheumatoid arthritis); DR2, DQw1 (associated with multiple sclerosis); DR3, DQw2 and DR7, DQw2 (associated with celiac disease); DR4, DQw3, and DR6, DQw (associated with pemphigus vulgaris); DR8 and DR5 (associated with pauciarticular juvenile rheumatoid arthritis); DR3, Dqw2, and DR2, DQw1 (associated with systemic lupus erythematosis); DR3 (associated with Sjogren's syndrome); DR2, DQw1 (associated with narcolepsy), DR3, DQw2 (associated with Graves' disease); and DR3, DQw2 (associated with dermatitis herpetiformis).

The peptide of interest is selected based upon the desired application. For example, to induce an immune reaction to a viral, fungal or bacterial infection or to a tumor, a peptide that is part of an antigen associated with the infectious agent or tumor may be selected. Peptides that are part of an autoreactive antigen may be selected to modify a T cell response in autoimmune disease. Self peptides which are presented by alloantigen may be selected to modify a T cell response associated with graft rejection or graft versus host (GVH) disease.

There is no limitation as to the peptides that may be used, provided that the peptide associates with the MHC element of the chimeric molecule such that the molecule is capable of binding to a T cell receptor. Binding of the chimeric molecule to a T cell receptor may be evaluated by methods known in the art, including fluorescence activated cell sorting (FACS) as described hereinbelow.

Examples of peptides of interest that may be incorporated into the molecules of the invention include those derived from glutamic acid decarboxylase 65 (associated with insulin dependent diabetes mellitus); myelin basic protein (associated with multiple sclerosis); human cartilage glucoprotein 39 (associated with rheumatoid arthritis); wheat gliadin (associated with celiac disease); and acetyl choline receptor (associated with myasthenia gravis).

Further, the peptides are not limited to peptides specifically involved in interaction with an antigen receptor and isolated from other peptide sequences, but rather also applies to peptides which comprise the portion which interacts with the antigen receptor, and may, in particular embodiments, constitute an entire native antigenic peptide or protein or an antigenic portion thereof. Without limitation, such peptides may be 5–30, and preferably 5–20 amino acids in length. Specific peptides of interest include, but are not limited to, peptides associated with multiple sclerosis such as PLP 38–49 (ALTGTEKLIETY; SEQ ID NO:1); PLE 91–104 (YTTGAVRQIFGDYK; SEQ ID NO:2); PLP 115–128 (TVTGGQKGRGSRGQ; SEQ ID NO:3); PLP 195–208 (SIGSLCADARMYGV; SEQ ID NO:4) (Kinkel et al., 1992, Neurology 42 (Suppl. 3): 159 (abstr. 87P); PLP 89–106 (GFYTTGAVRQIFGDYKTT; SEQ ID NO:5); PLP 40–60 (TGTEKLIETYFSKNYQDYEYL: SEQ ID NO:6) (Pelfrey et al., 1993, J. Neuroimmunol. 46:33–42; MBP 84–103 (Steinman et al., 1995, Mol. Med. Today 1:79–83); and p95–116 from PLP (Kawamura et al (2000) J. Clin. Invest. 105:977–984; and peptides associated with diabetes, such as proinsulin (1–24, 44–63 and 73–90); GAD65 (1–20, 21–40, 61–80, 126–140, 207–220, 231–250, 251–270, 261–280, 271–285, 281–300, 311–330, 361–380, 381–400, 471–490, 497–517, 509–528 and 521–285) (Rudy et al., 1995, Mol. Med. 1:625–633; Lohmann et al., 1996, J. Autoimmum. 9:385–389; Endl et al., 1997, J. Clin. Invest. 99:2405–2415) and p277 from heat shock protein 60 (Wicker et al. (1996) J. Clin. Invest. 98:8082.

In a preferred embodiment of the present invention, the chimeric molecule comprises: (a) an immunoglobulin constant region element having two chains covalently joined by a disulfide linkage, wherein the chains comprise the CH3 and CH2 and hinge domains; (b) two MHC class II elements comprising the extracellular domains of the α and β chains, wherein each of the MHC elements is covalently linked via the α or β chain to a chain of the immunoglobulin region constant element; and (c) a peptide of interest covalently linked to the MHC element or incorporated therein as a fusion protein.

The chimeric molecules used to make the multimeric complexes of the present invention may be made by assembling the components by known chemical methods, or by recombinant methodology. The sequences of nucleic acids encoding the elements of the chimeric molecules are known in the art and available in published literature and in databases such as GenBank. Those of ordinary skill in the art can construct nucleic acids encoding the chimeric molecules or portions thereof, which can be expressed and assembled or allowed to self-associate into the chimeric molecules. Nucleic acids encoding the peptide of interest may be incorporated into such constructs such that the peptide is provided as a fusion with the MHC element. Alternatively, the peptide may be subsequently covalently or non-covalently attached to the MHC element.

Chimeric molecules as described herein and methods of making such molecules are known in the art and disclosed for example by Casares et al. (1999) J. Exp. Med. 190:543–553; Casares et al. (1997) Protein Eng. 10:1295–1301; WO99/09064; WO93/10220; U.S. Pat. No. 6,197,302 B1; and U.S. Pat. No. 6,211,342 B1, the disclosures of which are incorporated by reference.

In a particularly preferred embodiment, the chimeric molecule comprises two MHC class II elements comprising the I-E$^d\alpha$ and I-E$^d\beta$ extracellular domains, each of which is covalently linked at the C-terminus of the I-E$^d\beta$ chain to one chain of an Fc$\gamma$2a fragment, and comprising a peptide of interest covalently linked to the N-terminus of the I-E$^d\beta$ chain.

The chimeric molecule may further comprise a toxin, such as ricin or diphtheria toxin. The toxin may be covalently or non-covalently linked to the MHC or immunoglobulin element of the chimeric molecule, or incorporated into a recombinant construct such that it is expressed as a part of a fusion protein in the chimeric molecule. The multimeric complexes are thus able to deliver the toxin to a specific T cell population, for example one implicated in autoimmune disease, resulting in destruction of the T cells.

Similarly, a drug with therapeutic utility in a T cell-mediated disorder, for example doxorubicin or cyclosporin A, can be covalently or non-covalently attached or fused to the chimeric molecule and delivered by the multimeric complex to target T cells. The toxins and drugs may be attached to the chimeric molecules by methods known in the art. The use of difunctional linkers for crosslinking, such as linear or branched PEGs, is specifically contemplated.

The multimeric complexes of the present invention comprise at least two chimeric molecules as described above and covalently linked through a carbohydrate residue of the immunoglobulin region element by a polyalkylene glycol linker.

Polyalkylene glycols and the use thereof to modify proteins are known in the art. In accordance with the present invention, a difunctional polyalkylene glycol, preferably a difunctional polyethylene glycol (PEG), is used to cross link the chimeric molecules via a carbohydrate residue on the immunoglobulin constant region element.

PEG (HO—(CH$_2$CH$_2$O)$_n$—CH$_2$CH$_2$—OH) is derivatized at both termini to provide activated difunctional PEG. Preferably PEG is modified to contain primary amino groups at both termini to provide diamino-PEG (NH$_2$—(CH$_2$CH$_2$O)$_n$—CH$_2$CH$_2$—NH$_2$). The molecular weight of the PEG is not limited but is preferably from 1000–5000, and more preferably about 3500. Diamino-PEG having a molecular weight of 3400 is commercially available from Shearwater Corporation (Huntsville, Ala.) and is particularly preferred in accordance with the present invention.

The chimeric molecules may be covalently linked through a carbohydrate residue of the immunoglobulin constant region by an enzymatic method as follows. The carbohydrate residue of the immunoglobulin constant regions of the chimeric molecules is desialylated by incubation with one or more neuraminidases. Free sialic acid (N-acetyl neuraminic N-acetyl acid, NANA) may be removed for example by dialysis. The desialylated molecules are reacted with galactose oxidase to oxidize the terminal galactose (Gal) residues, and with diamino-PEG. This reaction results in the formation of Schiff bases between the C6-aldehyde groups of the Gal residues and the amino terminal groups of the diamino-PEG. The Schiff bases may be stabilized by reductive alkylation, for example with pyridine borane. The resulting multimeric complexes may be purified by methods known in the art, including for example dialysis and size exclusion chromatography. Particularly preferred multimers, such as tetramers and octamers, may be identified and isolated by size exclusion chromatography.

In another embodiment, the present invention provides a method of making multimeric complexes of at least two chimeric molecules wherein the chimeric molecules comprise an immunoglobulin constant region element and two MHC elements associated with a peptide of interest, and wherein at least two of the chimeric molecules are covalently linked through a carbohydrate residue of the immunoglobulin constant region by a polyalkylene glycol linker.

The method comprises contacting the chimeric molecules with one or more neuraminidases under conditions to desialylate carbohydrate residues of the immunoglobulin constant region element to provide desialylated chimeric molecules, and contacting the desialylated chimeric molecules with galactose oxidase and diamino-polyalkylene glycol under conditions to covalently link two or more chimeric molecules.

In a preferred embodiment, the one or more neuraminidases are a mixture of neuraminidases from *Arthrobacter ureafaciens* and *Clostridium perfringens*. Following desialylation, free sialic acid may be removed, for example by dialysis.

In another preferred embodiment, the diamino-polyalkylene glycol is diamino-polyethylene glycol. In a particularly preferred embodiment, the diamino-polyethylene glycol has a molecular weight of about 3400 ((NH$_2$)$_2$-PEG$_{3,400}$, Shearwater Corporation, Huntsville, Ala.).

In another preferred embodiment, mild reducing conditions, for example treatment with pyridine borane, are used to stabilize the Schiff bases formed between the amino groups of PEG and the terminal galactose residues of the carbohydrate residues of the immunoglobulin constant region.

In another preferred embodiment, the resulting multimeric complexes are purified by methods known in the art, including for example size exclusion chromatography.

Conditions for desialylation and for derivatizing immunoglobulins with a monofunctional PEG derivative are disclosed in International Patent Application Publication Nos. WO96/40731 and WO96/36357, which disclosures provide reaction conditions and parameters that may be used in the practice of the present method. WO96/40731 and WO96/36357 are incorporated herein by reference.

In a particularly preferred embodiment, the present method comprises incubating the chimeric molecules overnight at 37° C. with neuraminidase from *Arthrobacter ureafaciens* and *Clostridium perfringens* (Calbiochem-Novobiochem Intern. Inc., La Jolla, Calif.) in 0.1 M phosphate buffer pH 5.5 containing 5 mM CaCl$_2$. Free sialic acid released by neuraminidase is removed by dialysis against PBS pH 7.4. Desialylated chimeric molecules are incubated for 48 hours at 37° C. with galactose oxidase (GAO, Sigma Chemical Co., St. Louis, Mo.) and diamino-polyethylene glycol bifunctional cross linker with a molecular mass of 3,400 Da ((NH$_2$)$_2$-PEG$_{3,400}$, Shearwater Corporation, Ala.). The Schiff bases formed between the aldehyde groups generated by GAO at the 6$^{th}$ carbon of terminal galactose residues and the amino groups of PEG are stabilized on mild reduction with 80 mM of pyridine borane (PB)(Aldrich). The reaction mixture is dialyzed against phosphate buffered saline (PBS) in SPECTRA/POR bags (100,000 MWCO, Sigma), and multimers are separated by size exclusion chromatography.

In accordance with the present invention it has been found that the enzymatically-mediated multimerization does not affect the ability of the chimeric molecules to bind specifically to a cognate TCR. The multimeric complexes of the present invention exhibit immunomodulatory effects on cognate T cells and are thus useful in the treatment of infectious and autoimmune disorders.

In another embodiment, the present invention provides a method of modulating T cell function comprising administering the multimeric complexes of the present invention to a subject. In the present method, the peptide of interest in the multimeric complex is one that is associated with a disease or disorder affecting the subject. For example, it is well-known in the art that specific autoantigens are associated with particular autoimmune diseases, and further, specific autoantigenic peptides have been identified. Accordingly, one of skill in the art can select a specific peptide for inclusion in the multimeric complex, and administer the multimeric complex to a subject affected by the disease state associated with the peptide. For example, and in a particularly preferred embodiment, a peptide derived from a glutamic acid decarboxylase 65 provides the peptide of interest in the multimeric complex. The complex is administered to a subject having Type I (insulin-dependent) diabetes, resulting in modulation of T cell function and amelioration of the diabetic condition. Other preferred embodiments include antigenic peptides derived from type-II collagen for use in the subject complexes for administration to a subject having rheumatoid arthritis, antigenic peptides from the acetyl choline receptor for use in the treatment of myasthenia gravis, and antigenic peptides from myelin basic protein for treatment of multiple sclerosis. Peptides derived from viral, bacterial and fungal proteins, or from tumor cells, may be used in the treatment of infection and cancer, respectively. In embodiments in which a toxin or drug is contained in the multimeric complex, the population of T cells mediating an autoimmune disease may be eliminated.

The present invention further provides a method of diagnosing an autoimmune disorder in a subject comprising isolating T cells from a subject and determining the number of T cells that react with a multimeric complex of the invention in which the peptide of interest is associated with the autoimmune disorder. In a preferred embodiment, the number of autoreactive T cells is determined by FACS.

In another embodiment, the present invention provides compositions comprising the multimeric complexes of the invention and a carrier. The term "carrier" as used herein includes any and all solvents, dispersion media, antibacterial and antifungal agents, microcapsules, liposomes, cationic lipid carriers, isotonic and absorption delaying agents and the like. The compositions may comprise the multimeric complexes in solid form, for example as a lyophilized preparation. Supplementary active ingredients may also be incorporated into the compositions and used in the methods of the present invention. The compositions may be formatted for convenient and effective administration in dosage unit form.

The dosage of the multimeric complexes may be such as to produce a local concentration of between about 0.01 and 10 μg/ml, and preferably between about 0.05 and 5 μg/ml. In specific nonlimiting embodiments of the invention, the dosage per kilogram may be between about 0.75 and 750 μg/kg, and preferably between about 3.75 and 375 μg/kg, and/or, for a human subject, between about 50 μg and 50 mg, and preferably between about 0.25 μg and 25 mg or between about 0.25 and 5 mg. The compositions of the invention may be administered to a subject orally, subcutaneously, intramuscularly, intravenously, intraarterially, intravaginally, intrarectally, intraperitaoneally, intrathecally, topically, or by inhalation. Sustained release formulations, including tissue or organ implants, may also be used.

All references cited herein are incorporated herein in their entirety.

The following nonlimiting examples serve to further illustrate the present invention.

EXAMPLE 1

Materials and Methods

The following materials and methods were used in subsequent examples.

Mice

Transgenic (Tg) BALB/c mice expressing the 14.3d TCR that recognizes the HA110-120 peptide of the hemagglutinin (HA) protein of PR8 influenza virus in association with I-E$^d$ class II molecules were provided by Dr. von Boehmer (Dana Farber Institute, MS). The seven to eight-week-old BALB/c mice were purchased from Jackson Laboratories, USA.

Cells

Primary T-cells specific for the immunodominant CD4 T cell epitope HA110-120 (TCR-HA T cells) were obtained from the spleens of Tg mice. Approximately 32% of T-cells in the spleen of these mice express the TCR-HA transgene as determined by fluorescence activated cell sorting (FACS) using 6.5.2 anti-TCR-HA clonotypic monoclonal antibody (mAb). The clonotypic 6.5.2 mAb (rat IgG1/k) was provided by Dr. J. Caton (NIH). The 14.3-1 T-cell hybridoma cells (TcH) expressing the 14.3d TCR-HA were provided by Dr. K. Karjalainen (Basel Institute for Immunology, Switzerland).

Soluble Bivalent MHC II-peptide Chimera

The genetically engineered soluble, bivalent MHC class II peptide chimera consists of the I-E$^d$α and I-E$^d$β extracellular domains that were dimerized through a murine Fcγ2a fragment at the C-termini of I-E$^d$β chains. The HA110-120 (SFERFEIFPKE, SEQ ID NO:7) CD4 T cell epitope of HA of influenza virus A/PR/8/34 (Haberman et al. (1990) J. Immunol. 145:3087) was covalently linked to the N-terminus of I-E$^d$β chains (Casares et al. (1997) Protein Engineering 10:1295–1301). The soluble, bivalent chimeric protein was chromatographically purified on a goat anti-mouse γ2a-Sepharose column from the cell culture supernatants of SF9 insect cells infected with baculovirus expressing both I-E$^d$α and I-E$^d$β/HA110-120/Fcγ2a genes, as previously described (Casares et al. (1997)). The soluble bivalent chimeric protein binds stably and specifically to cognate TCR on CD4$^+$ T-cells (Casares et al. (1997)).

Enzymatically-mediated synthesis of multimers

Soluble, bivalent chimeric protein (5 mg) was incubated overnight at 37° C. with 500 mU of neuraminidases from *Arthrobacter ureafaciens* and *Clostridium perfringens* (Calbiochem-Novobiochem Intern. Inc., La Jolla, Calif.) in 5 ml of 0.1 M phosphate buffer pH 5.5 containing 5 mM CaCl$_2$. Free sialic acid released by neuraminidases was removed by dialysis against phosphate buffered saline (PBS) pH 7.4. Desialylated bivalent chimeric protein was incubated for 48 hours at 37° C. with 100 U galactose oxidase (GAO, Sigma Chemical Co., St. Louis, Mo.) and 5 mg of diamino-polyethylene glycol bifunctional cross linker with a molecular mass of 3,400 Da (($NH_2$)2-$PEG_{3,400}$, Shearwater Corporation, AL). The Schiff bases formed between the aldehyde groups generated by GAO at the $6^{th}$ carbon of terminal galactose residues and the amino groups of PEG were stabilized on mild reduction with 80 mM of pyridine borane (PB)(Aldrich) (FIG. 1). The reaction mixture was dialyzed against PBS in SPECTRA/POR bags (100,000 MWCO, Sigma), and multimers were separated by size exclusion chromatography.

Chromatographic Separation of Multimeric Complexes

Multimers were separated by size-exclusion chromatography in a Superose 6 column (Amersham-Pharmacia Biotech) equilibrated in PBS. The reaction mixture (200μl) was applied in the column at 1 ml/min flow rate, and fractions were collected at 1 minute intervals. The recovery yield for each protein peak was calculated on the chromatographic profile using the UN-SCAN-IT analysis software version 5.1 (Silk Scientific Corp., CA). To identify the PEG polymer, some 0.025 ml from each fraction were reacted with 0.025 ml of Nessler's Reagent (Sigma). PEG polymer was detected as a whitish precipitate. The peak tubes were measured for the protein content using the Biuret microassay, since the Biuret reagent does not interfere with PEG polymers (Brumeanu et al. (1995) J. Immunol. 154:3088–3095).

SDS-PAGE and Western Blot Analyses

Some 5 μg of chromatographically purified multimers were electrophoresed in 4–12% polyacrylamide gradient gels (PhastGels, Amersham-Pharmacia, NJ) under denaturing and non-reducing conditions, and the gels were silver stained according to the manufacturer's instructions. In parallel experiments, 5 μl of blood serum and tissue extracts from mice injected intravenously (i.v.) with $^{125}$I-radiolabeled multimers were analyzed at various intervals of time by SDS-PAGE under denaturing and non-reducing conditions using 4–12% gradient PhastGels. Samples of tissue extracts containing $^{125}$I-labeled multimers were prepared from spleen, thymus, lymph nodes, and brain. The extracts were obtained by tissue homogenization, and then cleared of debris by centrifugation. The supernatants were collected and precipitated for 2 hours at room temperature with 50% of saturated ammonium sulfate (SAS), and the SAS precipitates were dialyzed extensively at 4° C. in SPECTRA/POR bags (100,000 MWCO) against PBS containing a cocktail of protein inhibitors (Complete kit, Boehringer Mannheim, Germany). The protein concentration in the dialyzed preparation was adjusted at 5 mg protein/ml with sample buffer containing 5% of 2-mercaptoethanol (2ME), and separated by SDS-PAGE in 4–12% gradient PhastGels. Gels were electrotransferred onto PVDF membranes (0.45 μm), and the radioactive bands were identified upon exposure of membranes onto Kodak X-OMAT films (Sigma).

The specificity of the glycosidic bonds generated by ($NH_2$)$_2$-$PEG_{3,400}$ linker between the N-glycan moieties of chimeric dimers was determined by Western blot. Samples of purified multimers (5 μg) were digested for 2 hours at 37° C. with PGNase F (0.01 U/μg protein, Sigma) in the presence of 5% 2ME, and electrophoresed on 10–15% gradient PhastGels. Gels were electrotransferred onto PVDF membranes (0.45 μm), and the membranes were blocked overnight at 4° C. with 5% fat free milk (Carnation, Nestle Food Company, Glendale, Calif.) in PBS, then washed with 0.05% Tween 20 in PBS, and incubated for 2 hours at room temperature with $^{125}$I-labeled goat anti-mouse γ2a Ab ($2 \times 10^5$ cpm/100 $cm^2$ membrane) in PBS containing 1% BSA and 0.05% Tween 20. The membranes were washed with 0.05% Tween 20 in PBS, and exposed onto Kodak X-OMAT films.

Cytoflurometric Analyses

The 14-3-1 TcH ($1 \times 10^5$) expressing 14.3d TCR-HA were incubated for 30 minutes on ice with 2 μg/ml of the purified multimers in PBS/BSA 1% containing or not 100 μg/ml 6.5.2 anti-TCR clonotypic mAb. Cells were washed in cold PBS/BSA 1% $NaN_3$ 0.05%, and bound multimeric molecules were stained for 30 minutes on ice with a goat anti-γ2a-FITC conjugate (Boehringer Mannheim). The fluorescence intensity was measured among 10,000 cells in a FACSCalibur instrument (Becton Dickinson, CA) after subtraction of the background generated by the secondary Ab-FITC conjugate. To determine the extent of apoptosis induced by the multimers in TCR-HA T-cells, two-color FACS analysis was used. Cells were stained for 30 minutes on ice with 2 μg of 6.5.2 clonotypic mAb-FITC conjugate and 2 μg of anti-Anexin V-PE conjugates (PharMingen, CA), and the 6.5.2$^+$/Anexin V$^+$ T-cells were scored among 10,000 events using the FACSCalibur instrument.

Thymidine Incorporation Assay

The proliferative capacity of TCR-HA T-cells on exposure to the multimers was determined by thymidine incorporation assay ($^3$H-TdR). Spleen cells ($10^6$) from TCR-HA Tg mice were incubated for 72 hours with various concentrations of purified multimers, or medium alone. Tritiated thymidine (1 μCi/well) was added to the cultures for the last 24 h, cells were harvested on filter paper (Squadron Inc., Sterling, Va.), and the radioactivity (cpm) was measured in a β-scintillation chamber (Amersham-Pharmacia Biotech).

Cytokine Assays

The cytokine production was determined in the cell culture supernatants of spleen cells ($10^6$) from Tg mice incubated for 48 hours with 10 μg/ml and 50 μg/ml of multimers. The amount of IL-2, IL-4, and IFN-γ was measured by ELISA according to the manufacturer's instructions (Cytoscreen mIL-2 and Cytoscreen mIL-4 ELISA kits, Biosource International, CA).

Blood Clearance and Organ Distribution

The multimers (100 μg in 100 μl of PBS) were radiolabeled with $^{125}$I using the conventional chloramine method. Two BALB/c mice per group were injected in the tail vein with $^{25}$I-labeled multimers ($50 \times 10^6$ cpm) in PBS (200 μl). The clearance rates and index of distribution in organs for the radiolabeled multimers were calculated as previously described (Brumeanu et al., 1995). Briefly, 15 minutes after injection, the time required for uniform distribution of the radiolabeled material, the mice were bled from the tail vein, and radioactivity (cpm) in 20 μl of serum was measured in a γ-counter (Pharmacia LKB). The total radioactivity injected per mouse (TRI) was estimated 15 minutes after injection, on the basis that 7.3% of body weight is blood and 55% of the blood volume is serum. The total residual radioactivity (TRR) was estimated in blood at the time of withdrawal. The index of distribution of multimers in the organs was expressed as a percent from TRR at the time of collection (% ID), according to the formula: % ID=1−(TRR/TRI)×100 (Brumeanu et al. (1995) J. Immunol. 154:3088–3095).

EXAMPLE 2

Characterization of Multimeric Complexes

Figure 2:
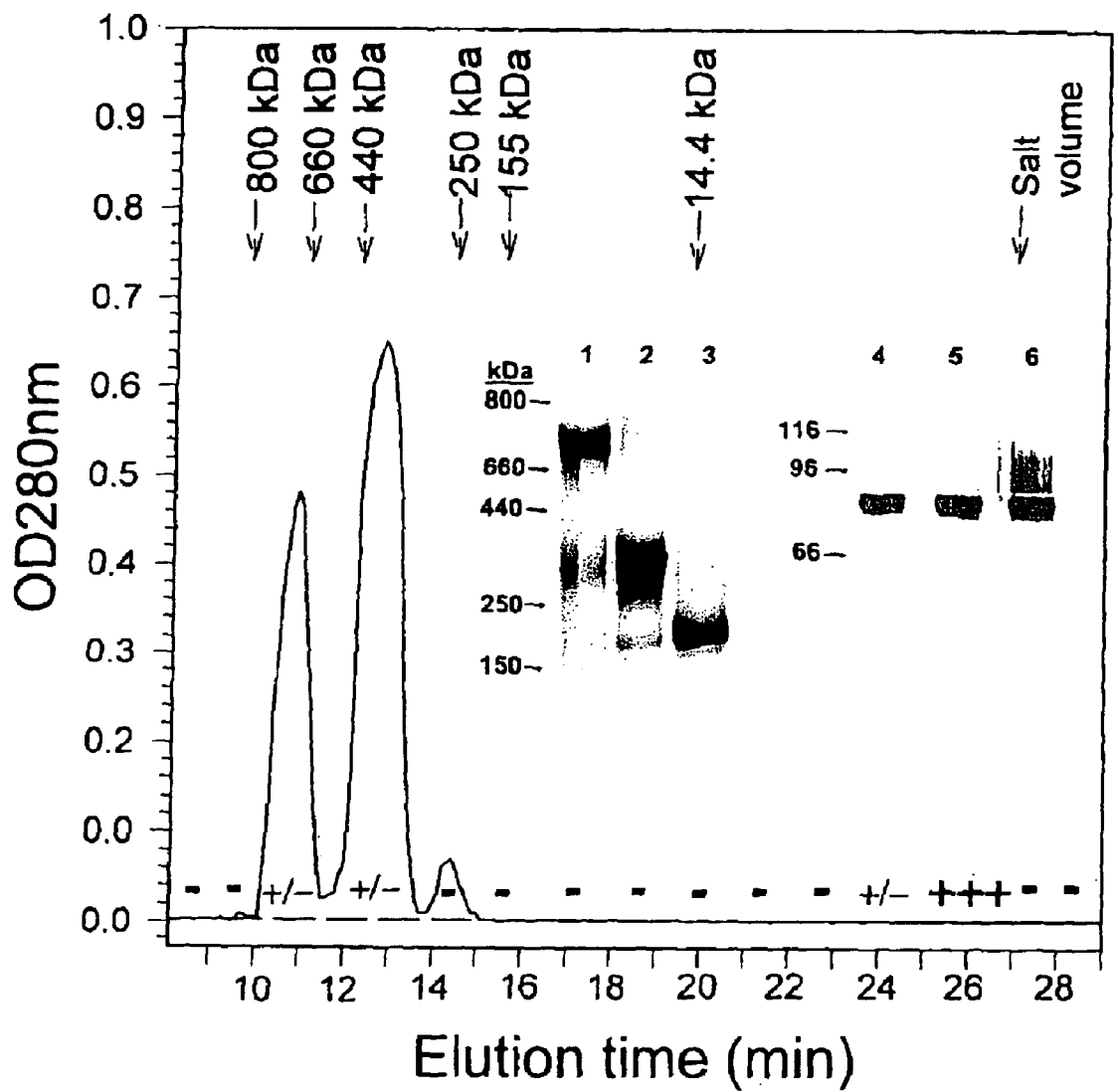
FIG. 2 depicts the separation of multimeric complexes by size exclusion chromatography and the characterization of the multimeric complexes.

Chimeric multimers synthesized as described in Example 1 were separated by size exclusion chromatography and characterized by SDS-PAGE and Western blot, the results of which are depicted in FIG. 2.

A superose 6 HR 10/30 column was calibrated at 1 min/ml with mouse IgM ($\geq$800 kDa), thyroglobulin (660 kDa), ferritin (440 kDa), catalase (250 kDa), mouse IgG (150 kDa), cytochrome c (14.4 kDa) in PBS. The mixture of multimers was dialyzed, applied on the column, and the tubes were collected at 1 minute intervals (continuous line). Each tube was tested for PEG presence by Nessler's reagent (negative reaction (−), weak positive reaction (±), and strong positive reaction (+). Some free, residual PEG polymer that was not dialyzed out eluted in the salt volume of the column (+).

The insert in FIG. 2 represents chromatographically purified multimers analyzed by SDS-PAGE under denaturing and non-reducing conditions (lane 1, octamer; lane 2, tetramer, and lane 3, dimer). Digestion with PGNase F under reducing conditions and identification with $^{125}$I-goat anti-γ2a Ab by Western blot revealed that multimers were composed of identical monomeric units of ~80 kDa (lane 4, octamer; lane 5, tetramer, and lane 6, dimer).

The foregoing results show that the enzymatically-mediated cross linking of chimeric dimers via diamino-PEG$_{3,400}$ polymer led mainly to the generation of tetramers and octamers as found by size exclusion chromatography. Their relative molecular masses estimated in the peak tubes were 375 kDa and 720 kDa, respectively. Quantification of the corresponding chromatographic peaks showed a yield recovery of 55% for tetramer, and 32.5% for octamer. Some 2% of highly multimerized complex (MW$\geq$800 kDa) and 9.5% of the dimer were also separated by chromatography. Accordingly, a small amount of dimer (9.5%) did not react with PEG polymer either because of less accessibility of the galactose acceptors, or because of less galactose acceptors per dimeric molecule. Using a galactose oxidase (GAO)/tolidine-horseradish peroxidase coupled assay, it was found that the number of galactose acceptors per molecule of dimer was on average 10.5. A small fraction of the dimers expressing lower amount of carbohydrates, which contained on the average 3.7 galactose acceptors per molecule, had previously been separated by anion-exchange chromatography (Casares et al. (1997) Protein Engineering 10:1295–1301). This may account for the lack of cross linking by PEG polymer for 9.5% of the dimers. The amount of PEG in the tetramer and octamer as detected by Nessler's reagent was considerably lower than in the peak of free PEG (MW$\leq$5 kDa). Lack of PEG in the peak of dimer and presence of PEG in the peaks of octamer and tetramer indicated that PEG did not co-elute with these proteins but rather was strongly attached to them.

The SDS-PAGE analysis confirmed the composition of the chromatographic peaks as consisting of multimers with molecular masses of 170 kDa for dimer, 365 kDa for tetramer, and 700 kDa for octamer (FIG. 2 insert, lanes 1, 2, and 30. Digestion of multimers with PGNase F under denaturing and reducing conditions followed by blotting with $^{125}$I-radiolabeled goat anti-γ2a Ab revealed a major component of ~80 kDa that corresponded to the monomeric unit of the dimer (FIG. 2 insert, lanes 4, 5, and 60. This clearly demonstrates that PEG polymer was able to covalently cross link the dimers through the N-glycan moieties. Together, the results demonstrate that: (1) the enzymatically-mediated cross linking of dimers by diamino-PEG$_{3,400}$ polymer generated covalently linked tetramers and octamers through their carbohydrate moieties, and (2) multimers can be efficiently cleared of residual adducts by size exclusion chromatography.

EXAMPLE 3

Binding of Multimeric Complexes to Cognate T-cells

The multimers of the previous examples were tested by FACS for their ability to bind to TCR-HA T-cells. The fluorescence intensity of 14-3-1 TcH expressing TCR-HA upon incubation with purified multimers and secondary Ab (goat anti-γ2a-FITC) was between 33.2 and 38.7%. The fact that differences in the fluorescence intensity of multimers were not detected suggests that either FACS analysis cannot distinguish discrete alterations in their affinity binding constants to cognate TCR, or the incorporated PEG cross linker in the multimers can interfere with the binding of secondary Ab. However, none of multimers bound to 14-3-1 TcH when the cells were preincubated with 6.5.2 clonotypic mAb. This clonotypic mAb inhibits the binding of the dimer to 14-3-1 TcH (Casares et al. (1999)). In aggregate, the results demonstrate that the enzymatically-mediated multimerization of the chimeric molecule did not affect its ability to bind specifically to cognate TCR.

EXAMPLE 4

Blood Clearance and Organ Distribution of Multimers

The multimers of the foregoing examples were tested in naïve BALB/c mice for their life span and stability in blood circulation and lymphoid organs.

Life span of multimers in blood circulation and distribution in the lymphoid organs were determined as follows. Chromatographically purified multimers were radiolabeled with $^{125}$Iodine, injected i.v. in naïve BALB/c mice, and the blood clearance, organ distribution, and the degradation patterns in blood and in lymphoid organs were determined as described. FIG. 3A shows the persistence of multimers in blood circulation; FIG. 3B shows the degradation patterns of multimers in blood circulation at various intervals of time after injection. Lane 1, $^{125}$I-labeled octamer before injection; lane 2, $^{125}$I-labeled octamer at 24 hours; lane 3, $^{125}$I-labeled octamer at 48 hours; lane 4, $^{125}$I-labeled octamer at 72 hours; lane 5, $^{125}$I-labeled octamer at 96 hours; lane 6, $^{125}$I-labeled tetramer before injection; lane 7, $^{125}$I-labeled tetramer at 24 hours; lane 8, $^{125}$I-labeled tetramer at 48 hours; lane 9, $^{125}$I-labeled tetramer at 72 hours; lane 10, $^{125}$I-labeled tetramer at 96 hours; lane 11, $^{125}$I-labeled dimer before injection; lane 12, $^{125}$I-labeled dimer at 24 hours; lane 13, $^{125}$I-labeled dimer at 48 hours; lane 14, $^{125}$I-labeled dimer at 72 hours; and lane 15, $^{125}$I-labeled dimer at 96 hours after injection. FIG. 3C shows the index of distribution (ID (%)) of multimers in lymphoid organs and brain. The bars represent the mean value per group of mice with a ±SD of 1.3% for spleen, 0.4% for lymph nodes, 1.4% for thymus, and 0.2% for brain. The bars marked for serum represent the % ID in serum 15 minutes after the i.v. injection, and they were assigned as the total radioactivity injection (% ID=100). The (%ID) values in organs were calculated in relation to the total radioactivity in blood as described. FIG. 3D illustrates the degradation patterns of multimers in the lymphoid organs, 48 hours after the i.v. administration. Lanes 1, 2, and 3, $^{125}$I-labeled octamer, tetramer, and dimer, respectively, in spleen homogenate. Lanes 4, 5, and 6, $^{125}$I-labeled octamer, tetramer, and dimer, respectively, in homogenates from lymph nodes. Lanes 7, 8, and 9, $^{125}$I-labeled octamer, tetramer, and dimer, respectively, in thymus homogenate.

All multimers showed longer half-life in blood circulation than a genetically engineered immunoglobulin (IgHA) expressing the HA110-120 peptide in the CDR3 loop of VH domain (Brumeanu et al. (1993) J. Exp. Med. 178:1795–1799). The half-life of multimers in blood was 50 hours (FIG. 3A). The electrophoretic analysis showed similar patterns of degradation of multimers in blood (FIG. 3B). During the first 24 hours there was no detectable degradation, whereas after 24 hours the degradation occurred progressively in all multimers. However, intact molecules of multimers were still detected 72 hours after injection.

Multimers were detected in spleen, lymph nodes and thymus (FIG. 3C) where they persisted as intact molecules for 48 hours after injection (FIG. 3D). However, the degradation process was slightly higher in spleen than in thymus and lymph nodes for all multimers, presumably because of APC's ability to uptake and process the proteins. None of multimers were detected in brain, indicating their inability to cross the hematoencephalic barrier. Longer life of multimers than the immunoglobulins in vivo may account for the high amount of carbohydrate moieties expressed by multimers. The persistence of multimers as intact molecules in blood and lymphoid organs also demonstrated that the PEG-galactose imidic bonds were resistant to endoglycosidases.

EXAMPLE 5

Immunoregulatory Effects of Multimers

Immunoregulatory Effects of Multimers on Cognate T-cells

The potency of multimers in stimulating cognate T-cells was compared at three different degrees of TCR/CD4 occupancy; 1, 10, and 50 µg/ml of multimer per $10^6$ splenic TCR-HA Tg cells. Since the frequency of TCR-HA T-cells in spleen of these mice is 30–33%, the TCR/CD4 occupancy corresponds respectively, to 0.7, 7.0, and 35 pMole multimer per cell.

The TCR-HA splenic T-cells from transgenic mice were exposed to the various concentrations of multimers for three days, and the $^3$H-TdR assay of thymidine incorporation in proliferating T-cells was determined as described hereinabove (FIG. 4A). At low occupancy (0.7 pMole/cell), octamer was one time more potent than tetramer, and 7 times more potent than dimer in stimulating TCR-HA T-cells (FIG. 4A). For as much as ten times higher occupancy (7.0 pMole/cell), there was an inverse relation between the valence and immunopotency of multimers. Thus, dimer was 1.5 times more potent than tetramer, whereas octamer did not stimulate the cells. At the highest occupancy (35 pMole/cell), none of ligands stimulated the cells.

The cytokine production was assessed in the cell culture supernatants after two days of continuous exposure to 10 µg/ml (FIG. 4B) and 50 µg/ml (FIG. 4C) of multimers. The cytokine values (pg/ml) are indicated as mean of duplicate wells. The ±SD for IL-2 measured in duplicate wells was 12.5 pg/ml, for IL-4 was 21 pg/ml, and for IFN-γ was 32.7 pg/ml.

The relation of valence-to-potency correlated with the pattern of cytokine secretion. At low TCR/CD4 occupancy, the valence of the multimeric paralleled the increase in IL-4 secretion (FIG. 4B), and at the highest occupancy where none of multimers stimulated the cells, the IL-2 and IL-4 secretion was barely detected. In contrast, the increase in valency paralleled the IFN-γ secretion (FIG. 4C).

TCR-HA Tg T-cells exposed for three days to 50 µg/ml of multimers under the conditions described for $^3$H-TdR assay were used to determine the percent of apoptosis by two-color FACS analysis using the 6.5.2 mAb-FITC and anti-Anexin V-PE conjugates as described. Results are shown in FIG. 5 (5A, control, 5B, dimer, 5C, tetramer, and 5D, octamer). The percentage of Anexin $V^+$ apoptotic cells within the gated population of $6.5.2^+$ cells (upper right corner) was calculated using the CELLQuest analysis software. [PANEL D?]

The increase in IFN-γ secretion correlated with a high percentage of apoptotic TCR-HA T-cells in the case of octamer, but not in the case of dimer and tetramer (FIG. 5). In contrast, the unresponsiveness of TCR-HA T-cells induced by dimer and tetramer at low and high TCR/CD4 occupancy was not due to apoptosis but rather to anergy, since the unresponsiveness of these cells was reverted by exogenous IL-2 added to the cultures.

The extent of T-cell unresponsiveness induced by multimers was correlated with the increase in IFN-γ secretion. Cells exposed to octamer at high TCR/CD4 occupancy underwent rapid apoptosis after secreting large amounts of IFN-γ.

The foregoing results indicated that depending on the degree of TCR/CD4 occupancy, the increase in valency correlated with distinct immunomodulatory effects on cognate T-cells. Thus, at low TCR occupancy, the increase in valency paralleled its potency to induce T-cell proliferation and Th2-like cytokine secretion, whereas at high occupancy was inversely proportional with the extent of T-cell unresponsiveness and cytokine secretion. The fact that multimers (1) exhibit long life in blood circulation, (2) penetrate the lymphoid organs, (3) persist in these organs as intact molecules for as long as 72 hours, and (4) exhibit immuno-modulatory effects on cognate T-cells demonstrate that this class of antigen-specific TCR/CD4 ligands can be used to modulate the effector functions of pathogenic T-cells in various infectious and autoimmune diseases. Also, the multimers are useful to identify antigen-specific $CD4^+$ memory T-cells that can persist in vivo for a long period of time at a low frequency.

We claim:

1. A multimeric complex of at least two chimeric molecules, wherein the chimeric molecules comprise an immunoglobulin constant region element and two MHC elements wherein each MHC element is associated with a peptide, and wherein the chimeric molecules are covalently linked through a carbohydrate residue of the immunoglobulin constant region element by a polyalkylene glycol linker; wherein each MHC element comprises all or part of an extracellular domain of an MHC molecule.

2. The multimeric complex of claim 1 comprising two chimeric molecules.

3. The multimeric complex of claim 1 comprising four chimeric molecules.

4. The multimeric complex of claim 1 wherein the immunoglobulin constant region element comprises the CH3, CH2 and hinge regions of two heavy chains and the chains are linked by at least one disulfide bond.

5. The multimeric complex of claim 1 wherein each MHC element comprises the extracellular domains of the α and β chains of an MHC class II molecule.

6. The multimeric complex of claim 1 wherein the peptide is part of an autoantigen.

7. The multimeric complex of claim 1 wherein the peptide is a diabetes autoantigen.

8. The multimeric complex of claim 1 further comprising a toxin.

9. The multimeric complex of claim 1 wherein the polyalkylene glycol linker is polyethylene glycol linker.

10. The multimeric complex of claim 9 wherein the polyethylene glycol linker is diamino polyethylene glycol linker.

11. The multimeric complex of claim 1 wherein the polyalkylene glycol linker is difunctional-polyalkylene glycol linker.

12. The multimeric complex of claim 11 wherein the difunctional-polyalkylene glycol linker is diamino-polyethylene glycol linker having a molecular weight of between about 1000–5000.

13. The multimeric complex of claim 11 wherein the difunctional-polyalkylene glycol linker is diamino-polyethylene glycol linker having a molecular weight of 3400.

14. A multimeric complex of at least two chimeric molecules wherein each chimeric molecule comprises: an immunoglobulin constant region element having two chains covalently joined by a disulfide linkage wherein the chains comprise the CH3, CH2 and hinge domains; two MHC class II elements comprising the extracellular domains of the α and β chains, wherein each of the MHC elements is covalently linked via the α or β chain to a chain of the immunoglobulin constant region element; and an associated peptide covalently linked or fused to the MHC element; and wherein the chimeric molecules are covalently linked through a carbohydrate residue of the immunoglobulin constant region element by a polyethylene glycol linker.

15. A composition comprising a multimeric complex of at least two chimeric molecules, wherein the chimeric molecules comprise an immunoglobulin constant region element and two MHC elements wherein each MHC element is associated with a peptide, and wherein the chimeric molecules are covalently linked through a carbohydrate residue of the immunoglobulin constant region element by a polyalkylene glycol linker; wherein each MHC element comprises all or part of an extracellular domain of an MHC molecule.

* * * * *

UNITED STATES PATENT AND TRADEMARK OFFICE
CERTIFICATE OF CORRECTION

| | |
|---|---|
| PATENT NO. | : 6,811,785 B2 |
| APPLICATION NO. | : 09/850336 |
| DATED | : November 2, 2004 |
| INVENTOR(S) | : Teodor D. Brumeanu et al. |

It is certified that error appears in the above-identified patent and that said Letters Patent is hereby corrected as shown below:

Please add the following government support clause immediately following the title in column 1; line 4

STATEMENT OF GOVERNMENT INTEREST

This invention was made with government support under Grant No. DK055461 awarded by the National Institutes of Health. The government has certain rights in the invention.

Signed and Sealed this
Eleventh Day of October, 2011

David J. Kappos
*Director of the United States Patent and Trademark Office*

SEQUENCE LISTING

<160> NUMBER OF SEQ ID NOS: 8

<210> SEQ ID NO 1
<211> LENGTH: 12
<212> TYPE: PRT
<213> ORGANISM: Homo sapiens

<400> SEQUENCE: 1

Ala Leu Thr Gly Thr Glu Lys Leu Ile Glu Thr Tyr
1               5                   10

<210> SEQ ID NO 2
<211> LENGTH: 14
<212> TYPE: PRT
<213> ORGANISM: Homo sapiens

<400> SEQUENCE: 2

Tyr Thr Thr Gly Ala Val Arg Gln Ile Phe Gly Asp Tyr Lys
1               5                   10

<210> SEQ ID NO 3
<211> LENGTH: 14
<212> TYPE: PRT
<213> ORGANISM: Homo sapiens

<400> SEQUENCE: 3

Thr Val Thr Gly Gly Gln Lys Gly Arg Gly Ser Arg Gly Gln
1               5                   10

<210> SEQ ID NO 4
<211> LENGTH: 14
<212> TYPE: PRT
<213> ORGANISM: Homo sapiens

<400> SEQUENCE: 4

Ser Ile Gly Ser Leu Cys Ala Asp Ala Arg Met Tyr Gly Val
1               5                   10

<210> SEQ ID NO 5
<211> LENGTH: 18
<212> TYPE: PRT
<213> ORGANISM: Homo sapiens

<400> SEQUENCE: 5

Gly Phe Tyr Thr Thr Gly Ala Val Arg Gln Ile Phe Gly Asp Tyr Lys
1               5                   10                  15

Thr Thr

<210> SEQ ID NO 6
<211> LENGTH: 21
<212> TYPE: PRT
<213> ORGANISM: Homo sapiens

<400> SEQUENCE: 6

Thr Gly Thr Glu Lys Leu Ile Glu Thr Tyr Phe Ser Lys Asn Tyr Gln
1               5                   10                  15

Asp Tyr Glu Tyr Leu
            20

<210> SEQ ID NO 7
<211> LENGTH: 11
<212> TYPE: PRT
<213> ORGANISM: Influenza

<400> SEQUENCE: 7

Ser Phe Glu Arg Phe Glu Ile Phe Pro Lys Glu
1               5                   10

-continued

```
<210> SEQ ID NO 8
<211> LENGTH:
<212> TYPE:
<213> ORGANISM:

<400> SEQUENCE: 8

000
```